United States Patent [19]
Lee et al.

[11] Patent Number: 6,080,382
[45] Date of Patent: *Jun. 27, 2000

[54] ZEOLITE SSZ-48

[75] Inventors: Gregory S. Lee, San Ramon; Stacey I. Zones, San Francisco, both of Calif.

[73] Assignee: Chevron U. S. A. Inc., San Francisco, Calif.

[ * ] Notice: This patent is subject to a terminal disclaimer.

[21] Appl. No.: 08/992,520

[22] Filed: Dec. 17, 1997

Related U.S. Application Data

[60] Provisional application No. 60/034,833, Dec. 31, 1996.

[51] Int. Cl.⁷ ............ C01B 39/48; C01B 39/06; C01B 39/12

[52] U.S. Cl. ............ 423/706; 423/713; 423/718; 423/212; 423/239.2; 208/111.01; 208/27; 208/134; 208/137; 208/138; 208/89; 585/467; 585/475; 585/481; 585/533

[58] Field of Search ................. 423/706, 713, 423/718, 212, 239.2; 208/111.01, 27, 134, 137, 138, 89; 585/467, 475, 481, 533

[56] References Cited

U.S. PATENT DOCUMENTS

| | | | |
|---|---|---|---|
| 3,567,372 | 3/1971 | Duecker et al. | 423/718 |
| 4,526,767 | 7/1985 | Robinson et al. . | |
| 4,826,667 | 5/1989 | Zones et al. | 423/718 |
| 4,855,270 | 8/1989 | Haddad et al. | 423/706 |
| 5,174,981 | 12/1992 | Hellring et al. | 423/718 |
| 5,236,575 | 8/1993 | Bennett et al. | 423/718 |
| 5,580,540 | 12/1996 | Nakagawa et al. | 423/718 |
| 5,965,104 | 10/1999 | Lee et al. | 423/706 |

FOREIGN PATENT DOCUMENTS

| | | | |
|---|---|---|---|
| 0197775A2 | 10/1986 | European Pat. Off. | C01B 33/28 |
| 96/01688 | 1/1996 | WIPO | B01J 29/00 |

*Primary Examiner*—Mark L. Bell
*Assistant Examiner*—David Sample
*Attorney, Agent, or Firm*—A. Stephen Zavell; Richard J. Sheridan; W. Keith Turner

[57] ABSTRACT

The present invention relates to new crystalline zeolite SSZ-48 prepared using a decahydroquinolinium cation templating agent.

70 Claims, No Drawings

ZEOLITE SSZ-48

This application claims the benefit of provisional application Ser. No. 60/034,833 filed Dec. 31, 1996.

BACKGROUND OF THE INVENTION

1. Field of the Invention

The present invention relates to new crystalline zeolite SSZ-48, a method for preparing SSZ-48 using a decahydroquinolinium cation templating agent, and processes employing SSZ-48 as a catalyst.

2. State of the Art

Because of their unique sieving characteristics, as well as their catalytic properties, crystalline molecular sieves and zeolites are especially useful in applications such as hydrocarbon conversion, gas drying and separation. Although many different crystalline molecular sieves have been disclosed, there is a continuing need for new zeolites with desirable properties for gas separation and drying, hydrocarbon and chemical conversions, and other applications. New zeolites may contain novel internal pore architectures, providing enhanced selectivities in these processes.

Crystalline aluminosilicates are usually prepared from aqueous reaction mixtures containing alkali or alkaline earth metal oxides, silica, and alumina. Crystalline borosilicates are usually prepared under similar reaction conditions except that boron is used in place of aluminum. By varying the synthesis conditions and the composition of the reaction mixture, different zeolites can often be formed.

SUMMARY OF THE INVENTION

The present invention is directed to a family of crystalline molecular sieves with unique properties, referred to herein as "zeolite SSZ-48" or simply "SSZ-48". Preferably, SSZ-48 is obtained in its silicate, aluminosilicate, titanosilicate, vanadosilicate or borosilicate form. The term "silicate" refers to a zeolite having a high mole ratio of silicon oxide relative to aluminum oxide, preferably a mole ratio greater than 100. As used herein, the term "aluminosilicate" refers to a zeolite containing both alumina and silica and the term "borosilicate" refers to a zeolite containing oxides of both boron and silicon.

In accordance with this invention, there is also provided a zeolite having a mole ratio greater than about 40 of an oxide of a first tetravalent element to an oxide of a second tetravalent element different from said first tetravalent element, trivalent element, pentavalent element or mixture thereof and having, after calcination, the X-ray diffraction lines of Table II.

Further, in accordance with this invention, there is provided a zeolite having a mole ratio greater than about 40 of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof and having, after calcination, the X-ray diffraction lines of Table II below.

The present invention further provides such a zeolite having a composition, as synthesized and in the anhydrous state, in terms of mole ratios as follows:

| | |
|---|---|
| $YO_2/W_cO_d$ | 40–100 |
| $M_{2/n}/YO_2$ | 0.01–0.03 |
| $Q/YO_2$ | 0.02–0.05 | wherein Y is silicon, germanium or a mixture thereof; W is aluminum, gallium, iron, boron, titanium, indium, vanadium or mixtures thereof; c is 1 or 2; d is 2 when c is 1 (i.e., W is tetravalent) or d is 3 or 5 when c is 2 (i.e., d is 3 when W is trivalent or 5 when W is pentavalent); M is an alkali metal cation, alkaline earth metal cation or mixtures thereof; n is the valence of M (i.e., 1 or 2); and Q is at least one decahydroquinolinium cation.

In accordance with this invention, there is also provided a zeolite prepared by thermally treating a zeolite having a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 40 at a temperature of from about 200° C. to about 800° C., the thus-prepared zeolite having the X-ray diffraction lines of Table II. The present invention also includes this thus-prepared zeolite which is predominantly in the hydrogen form, which hydrogen form is prepared by ion exchanging with an acid or with a solution of an ammonium salt followed by a second calcination.

Also provided in accordance with the present invention is a method of preparing a crystalline material comprising an oxide of a first tetravalent element and an oxide of a second tetravalent element which is different from said first tetravalent element, trivalent element, pentavalent element or mixture thereof, said method comprising contacting under crystallization conditions sources of said oxides and a templating agent comprising a decahydroquinolinium cation.

The present invention additionally provides a process for converting hydrocarbons comprising contacting a hydrocarbonaceous feed at hydrocarbon converting conditions with a catalyst comprising the zeolite of this invention. The zeolite may be predominantly in the hydrogen form. It may also be substantially free of acidity.

Further provided by the present invention is a hydrocracking process comprising contacting a hydrocarbon feedstock under hydrocracking conditions with a catalyst comprising the zeolite of this invention, preferably predominantly in the hydrogen form.

This invention also includes a dewaxing process comprising contacting a hydrocarbon feedstock under dewaxing conditions with a catalyst comprising the zeolite of this invention, preferably predominantly in the hydrogen form.

The present invention also includes a process for improving the viscosity index of a dewaxed product of waxy hydrocarbon feeds comprising contacting the waxy hydrocarbon feed under isomerization dewaxing conditions with a catalyst comprising the zeolite of this invention, preferably predominantly in the hydrogen form.

The present invention further includes a process for producing a $C_{20+}$ lube oil from a $C_{20+}$ olefin feed comprising isomerizing said olefin feed under isomerization conditions over a catalyst comprising at least one Group VIII metal and the zeolite of this invention. The zeolite may be predominantly in the hydrogen form.

In accordance with this invention, there is also provided a process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi with a catalyst comprising at least one Group VIII metal and the zeolite of this invention, preferably predominantly in the hydrogen form. The catalyst may be a layered catalyst comprising a first layer comprising at least one Group VIII metal and the zeolite of this invention, and a second layer comprising an aluminosilicate zeolite which is more shape selective than the zeolite of said first layer.

Also included in the present invention is a process for preparing a lubricating oil which comprises hydrocracking in a hydrocracking zone a hydrocarbonaceous feedstock to obtain an effluent comprising a hydrocracked oil, and catalytically dewaxing said effluent comprising hydrocracked oil at a temperature of at least about 400° F. and at a pressure of from about 15 psig to about 3000 psig in the presence of added hydrogen gas with a catalyst comprising at least one Group VIII metal and the zeolite of this invention. The zeolite may be predominantly in the hydrogen form.

Further included in this invention is a process for isomerization dewaxing a raffinate comprising contacting said raffinate in the presence of added hydrogen with a catalyst comprising at least one Group VIII metal and the zeolite of this invention. The raffinate may be bright stock, and the zeolite may be predominantly in the hydrogen form.

Also included in this invention is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C., under aromatic conversion conditions with a catalyst comprising the zeolite of this invention made substantially free of acidity by neutralizing said zeolite with a basic metal. Also provided in this invention is such a process wherein the zeolite contains a Group VIII metal component.

Also provided by the present invention is a catalytic cracking process comprising contacting a hydrocarbon feedstock in a reaction zone under catalytic cracking conditions in the absence of added hydrogen with a catalyst comprising the zeolite of this invention, preferably predominantly in the hydrogen form. Also included in this invention is such a catalytic cracking process wherein the catalyst additionally comprises a large pore crystalline cracking component.

This invention further provides an isomerization process for isomerizing $C_4$ to $C_7$ hydrocarbons, comprising contacting a feed having normal and slightly branched $C_4$ to $C_7$ hydrocarbons under isomerizing conditions with a catalyst comprising the zeolite of this invention, preferably predominantly in the hydrogen form. The zeolite may be impregnated with at least one Group VIII metal, preferably platinum. The catalyst may be calcined in a steam/air mixture at an elevated temperature after impregnation of the Group VIII metal.

Also provided by the present invention is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of a catalyst comprising the zeolite of this invention, preferably predominantly in the hydrogen form. The olefin may be a $C_2$ to $C_4$ olefin, and the aromatic hydrocarbon and olefin may be present in a molar ratio of about 4:1 to about 20:1, respectively. The aromatic hydrocarbon may be selected from the group consisting of benzene, toluene, ethylbenzene, xylene, or mixtures thereof.

Further provided in accordance with this invention is a process for transalkylating an aromatic hydrocarbon which comprises contacting under transalkylating conditions an aromatic hydrocarbon with a polyalkyl aromatic hydrocarbon under at least partial liquid phase conditions and in the presence of a catalyst comprising the zeolite of this invention, preferably predominantly in the hydrogen form. The aromatic hydrocarbon and the polyalkyl aromatic hydrocarbon may be present in a molar ratio of from about 1:1 to about 25:1, respectively. The aromatic hydrocarbon may be selected from the group consisting of benzene, toluene, ethylbenzene, xylene, or mixtures thereof, and the polyalkyl aromatic hydrocarbon may be a dialkylbenzene.

Further provided by this invention is a process to convert paraffins to aromatics which comprises contacting paraffins under conditions which cause paraffins to convert to aromatics with a catalyst comprising the zeolite of this invention, said catalyst comprising gallium, zinc, or a compound of gallium or zinc.

In accordance with this invention there is also provided a process for isomerizing olefins comprising contacting said olefin under conditions which cause isomerization of the olefin with a catalyst comprising the zeolite of this invention.

Further provided in accordance with this invention is a process for isomerizing an isomerization feed comprising an aromatic $C_8$ stream of xylene isomers or mixtures of xylene isomers and ethylbenzene, wherein a more nearly equilibrium ratio of ortho-, meta- and para-xylenes is obtained, said process comprising contacting said feed under isomerization conditions with a catalyst comprising the zeolite of this invention.

The present invention further provides a process for oligomerizing olefins comprising contacting an olefin feed under oligomerization conditions with a catalyst comprising the zeolite of this invention.

This invention also provides a process for converting lower alcohols and other oxygenated hydrocarbons comprising contacting said lower alcohol or other oxygenated hydrocarbon with a catalyst comprising the zeolite of this invention under conditions to produce liquid products.

Also provided by the present invention is an improved process for the reduction of oxides of nitrogen contained in a gas stream in the presence of oxygen wherein said process comprises contacting the gas stream with a zeolite, the improvement comprising using as the zeolite a zeolite having a mole ratio greater than about 40 of an oxide of a first tetravalent element to an oxide of a second tetravalent element different from said first tetravalent element, trivalent element, pentavalent element or mixture thereof and having, after calcination, the X-ray diffraction lines of Table II. The zeolite may contain a metal or metal ions (such as cobalt, copper or mixtures thereof) capable of catalyzing the reduction of the oxides of nitrogen, and may be conducted in the presence of a stoichiometric excess of oxygen. In a preferred embodiment, the gas stream is the exhaust stream of an internal combustion engine.

DETAILED DESCRIPTION OF THE INVENTION

The present invention comprises a family of crystalline, large pore zeolites designated herein "zeolite SSZ-48" or simply "SSZ-48". As used herein, the term "large pore" means having an average pore size diameter greater than about 6.0 Angstroms, preferably from about 6.5 Angstroms to about 7.5 Angstroms.

In preparing SSZ-48 zeolites, a decahydroquinolinium cation is used as a crystallization template. The decahydroquinolinium cation may have the following structure:

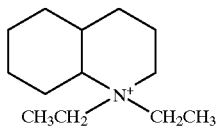

The anion (X⁻) associated with the cation may be any anion which is not detrimental to the formation of the zeolite. Representative anions include halogen, e.g., fluoride, chloride, bromide and iodide, hydroxide, acetate, sulfate, tetrafluoroborate, carboxylate, and the like. Hydroxide is the most preferred anion.

In general, SSZ-48 is prepared by contacting an active source of one or more oxides selected from the group consisting of monovalent element oxides, divalent element oxides, trivalent element oxides, and tetravalent element oxides with the decahydroquinolinium cation templating agent.

SSZ-48 is prepared from a reaction mixture having the composition shown in Table A below.

TABLE A

|  | Reaction Mixture | |
| --- | --- | --- |
|  | Typical | Preferred |
| $YO_2/W_aO_b$ | 10–100 | 15–40 |
| OH—/$YO_2$ | 0.10–0.50 | 0.20–0.30 |
| Q/$YO_2$ | 0.05–0.50 | 0.10–0.20 |
| $M_{2/n}/YO_2$ | 0.01–0.10 | 0.03–0.07 |
| $H_2O/YO_2$ | 20–80 | 30–45 | where Y, W, Q, M and n are as defined above, and a is 1 or 2, and b is 2 when a is 1 (i.e., W is tetravalent) and b is 3 when a is 2 (i.e., W is trivalent).

In practice, SSZ-48 is prepared by a process comprising:
 (a) preparing an aqueous solution containing sources of at least one oxide capable of forming a crystalline molecular sieve and a decahydroquinolinium cation having an anionic counterion which is not detrimental to the formation of SSZ-48;
 (b) maintaining the aqueous solution under conditions sufficient to form crystals of SSZ-48; and
 (c) recovering the crystals of SSZ-48.

Accordingly, SSZ-48 may comprise the crystalline material and the templating agent in combination with metallic and non-metallic oxides bonded in tetrahedral coordination through shared oxygen atoms to form a cross-linked three dimensional crystal structure. The metallic and non-metallic oxides comprise one or a combination of oxides of a first tetravalent element(s), and one or a combination of a second tetravalent element(s) different from the first tetravalent element(s), trivalent element(s), pentavalent element(s) or mixture thereof. The first tetravalent element(s) is preferably selected from the group consisting of silicon, germanium and combinations thereof. More preferably, the first tetravalent element is silicon. The second tetravalent element (which is different from the first tetravalent element), trivalent element and pentavalent element is preferably selected from the group consisting of aluminum, gallium, iron, boron, titanium, indium, vanadium and combinations thereof. More preferably, the second trivalent or tetravalent element is aluminum or boron.

Typical sources of aluminum oxide for the reaction mixture include aluminates, alumina, aluminum colloids, aluminum oxide coated on silica sol, hydrated alumina gels such as Al(OH)3 and aluminum compounds such as $AlC_3$ and $Al_2(SO_4)_3$. Typical sources of silicon oxide include silicates, silica hydrogel, silicic acid, fumed silica, colloidal silica, tetra-alkyl orthosilicates, and silica hydroxides. Boron, as well as gallium, germanium, titanium, indium, vanadium and iron, can be added in forms corresponding to their aluminum and silicon counterparts.

A source zeolite reagent may provide a source of aluminum or boron. In most cases, the source zeolite also provides a source of silica. The source zeolite in its dealuminated or deboronated form may also be used as a source of silica, with additional silicon added using, for example, the conventional sources listed above. Use of a source zeolite reagent as a source of alumina for the present process is more completely described in U.S. Pat. No. 5,187,132, issued Feb. 16, 1993 to Zones et al. entitled "Preparation of Borosilicate Zeolites", the disclosure of which is incorporated herein by reference.

Typically, an alkali metal hydroxide and/or an alkaline earth metal hydroxide, such as the hydroxide of sodium, potassium, lithium, cesium, rubidium, calcium, and magnesium, is used in the reaction mixture; however, this component can be omitted so long as the equivalent basicity is maintained. The templating agent may be used to provide hydroxide ion. Thus, it may be beneficial to ion exchange, for example, the halide for hydroxide ion, thereby reducing or eliminating the alkali metal hydroxide quantity required. The alkali metal cation or alkaline earth cation may be part of the as-synthesized crystalline oxide material, in order to balance valence electron charges therein.

The reaction mixture is maintained at an elevated temperature until the crystals of the SSZ-48 zeolite are formed. The hydrothermal crystallization is usually conducted under autogenous pressure, at a temperature between 100° C. and 200° C., preferably between 135° C. and 160° C. The crystallization period is typically greater than 1 day and preferably from about 3 days to about 20 days.

Preferably, the zeolite is prepared using mild stirring or agitation.

During the hydrothermal crystallization step, the SSZ-48 crystals can be allowed to nucleate spontaneously from the reaction mixture. The use of SSZ-48 crystals as seed material can be advantageous in decreasing the time necessary for complete crystallization to occur. In addition, seeding can lead to an increased purity of the product obtained by promoting the nucleation and/or formation of SSZ-48 over any undesired phases. When used as seeds, SSZ-48 crystals are added in an amount between 0.1 and 10% of the weight of silica used in the reaction mixture.

Once the zeolite crystals have formed, the solid product is separated from the reaction mixture by standard mechanical separation techniques such as filtration. The crystals are water-washed and then dried, e.g., at 90° C. to 150° C. for from 8 to 24 hours, to obtain the as-synthesized SSZ-48 zeolite crystals. The drying step can be performed at atmospheric pressure or under vacuum.

SSZ-48 as prepared has a mole ratio of an oxide selected from silicon oxide, germanium oxide and mixtures thereof to an oxide selected from aluminum oxide, gallium oxide, iron oxide, boron oxide, titanium oxide, indium oxide, vanadium oxide and mixtures thereof greater than about 40; and has the X-ray diffraction lines of Table I below. SSZ-48 further has a composition, as synthesized and in the anhydrous state, in terms of mole ratios, shown in Table B below.

TABLE B

| As-Synthesized SSZ-48 | |
| --- | --- |
| $YO_2/W_cO_d$ | 40–100 |
| $M_{2/n}/YO_2$ | 0.01–0.03 |
| $Q/YO_2$ | 0.02–0.05 | where Y, W, c, d, M and Q are as defined above.

A method of increasing the mole ratio of silica to boron is by using standard acid leaching or chelating treatments.

Lower silica to alumina ratios may also be obtained by using methods which insert aluminum into the crystalline framework. For example, aluminum insertion may occur by thermal treatment of the zeolite in combination with an alumina binder or dissolved source of alumina. Such procedures are described in U.S. Pat. No. 4,559,315, issued on Dec. 17, 1985 to Chang et al.

It is believed that SSZ-48 is comprised of a new framework structure or topology which is characterized by its X-ray diffraction pattern. SSZ-48 zeolites, as-synthesized, have a crystalline structure whose X-ray powder diffraction pattern exhibit the characteristic lines shown in Table I and is thereby distinguished from other known zeolites.

TABLE I

As-Synthesized SSZ-48

| 2 Theta[a] | d | Relative Intensity[b] |
| --- | --- | --- |
| 6.55 | 13.5 | S |
| 8.0 | 11.0 | VS |
| 9.4 | 9.40 | M |
| 11.3 | 7.82 | M–W |
| 20.05 | 4.42 | VS |
| 22.7 | 3.91 | VS |
| 24.1 | 3.69 | VS |
| 26.5 | 3.36 | S |
| 27.9 | 3.20 | S |
| 35.85 | 2.50 | M |

[a] ±0.3
[b] The X-ray patterns provided are based on a relative intensity scale in which the strongest line in the X-ray pattern is assigned a value of 100: W(weak) is less than 20; M(medium) is between 20 and 40; S(strong) is between 40 and 60; VS(very strong) is greater than 60.

After calcination, the SSZ-48 zeolites have a crystalline structure whose X-ray powder diffraction pattern include the characteristic lines shown in Table II:

TABLE II

Calcined SSZ-48

| 2 Theta[a] | d | Relative Intensity[b] |
| --- | --- | --- |
| 6.55 | 13.5 | VS |
| 8.0 | 11.0 | VS |
| 9.4 | 9.40 | S |
| 11.3 | 7.82 | M |
| 20.05 | 4.42 | M |
| 22.7 | 3.91 | M |
| 24.1 | 3.69 | M |
| 26.5 | 3.36 | M |
| 27.9 | 3.20 | W |
| 35.85 | 2.50 | W |

[a] ±0.3

The X-ray powder diffraction patterns were determined by standard techniques. The radiation was the K-alpha/doublet of copper. The peak heights and the positions, as a function of 2θ where θ is the Bragg angle, were read from the relative intensities of the peaks, and d, the interplanar spacing in Angstroms corresponding to the recorded lines, can be calculated.

The variation in the scattering angle (two theta) measurements, due to instrument error and to differences between individual samples, is estimated at ±0.30 degrees.

The X-ray diffraction pattern of Table I is representative of "as-synthesized" or "as-made" SSZ-48 zeolites. Minor variations in the diffraction pattern can result from variations in the silica-to-alumina or silica-to-boron mole ratio of the particular sample due to changes in lattice constants. In addition, sufficiently small crystals will affect the shape and intensity of peaks, leading to significant peak broadening.

Representative peaks from the X-ray diffraction pattern of calcined SSZ-48 are shown in Table II. Calcination can also result in changes in the intensities of the peaks as compared to patterns of the "as-made" material, as well as minor shifts in the diffraction pattern. The zeolite produced by exchanging the metal or other cations present in the zeolite with various other cations (such as $H^+$ or $NH_4^+$) yields essentially the same diffraction pattern, although again, there may be minor shifts in the interplanar spacing and variations in the relative intensities of the peaks. Notwithstanding these minor perturbations, the basic crystal lattice remains unchanged by these treatments.

Crystalline SSZ-48 can be used as-synthesized, but preferably will be thermally treated (calcined). Usually, it is desirable to remove the alkali metal cation by ion exchange and replace it with hydrogen, ammonium, or any desired metal ion. The zeolite can be leached with chelating agents, e.g., EDTA or dilute acid solutions, to increase the silica to alumina mole ratio. The zeolite can also be steamed; steaming helps stabilize the crystalline lattice to attack from acids.

The zeolite can be used in intimate combination with hydrogenating components, such as tungsten, vanadium molybdenum, rhenium, nickel cobalt, chromium, manganese, or a noble metal, such as palladium or platinum, for those applications in which a hydrogenation-dehydrogenation function is desired.

Metals may also be introduced into the zeolite by replacing some of the cations in the zeolite with metal cations via standard ion exchange techniques (see, for example, U.S. Pat. Nos. 3,140,249 issued Jul. 7, 1964 to Plank et al.; 3,140,251 issued Jul. 7, 1964 to Plank et al.; and 3,140,253 issued Jul. 7, 1964 to Plank et al.). Typical replacing cations can include metal cations, e.g., rare earth, Group IA, Group IIA and Group VIII metals, as well as their mixtures. Of the replacing metallic cations, cations of metals such as rare earth, Mn, Ca, Mg, Zn, Cd, Pt, Pd, Ni, Co, Ti, Al, Sn, and Fe are particularly preferred.

The hydrogen, ammonium, and metal components can be ion-exchanged into the SSZ-48. The zeolite can also be impregnated with the metals, or, the metals can be physically and intimately admixed with the zeolite using standard methods known to the art.

Typical ion-exchange techniques involve contacting the synthetic zeolite with a solution containing a salt of the desired replacing cation or cations. Although a wide variety of salts can be employed, chlorides and other halides, acetates, nitrates, and sulfates are particularly preferred. The zeolite is usually calcined prior to the ion-exchange procedure to remove the organic matter present in the channels and on the surface, since this results in a more effective ion exchange. Representative ion exchange techniques are disclosed in a wide variety of patents including U.S. Pat. Nos. 3,140,249 issued on Jul. 7, 1964 to Plank et al.; 3,140,251 issued on Jul. 7, 1964 to Plank et al.; and 3,140,253 issued on Jul. 7, 1964 to Plank et al.

Following contact with the salt solution of the desired replacing cation, the zeolite is typically washed with water and dried at temperatures ranging from 65° C. to about 200° C. After washing, the zeolite can be calcined in air or inert gas at temperatures ranging from about 200° C. to about 800° C. for periods of time ranging from 1 to 48 hours, or more, to produce a catalytically active product especially useful in hydrocarbon conversion processes.

Regardless of the cations present in the synthesized form of SSZ-48, the spatial arrangement of the atoms which form the basic crystal lattice of the zeolite remains essentially unchanged.

SSZ-48 can be formed into a wide variety of physical shapes. Generally speaking, the zeolite can be in the form of a powder, a granule, or a molded product, such as extrudate having a particle size sufficient to pass through a 2-mesh (Tyler) screen and be retained on a 400-mesh (Tyler) screen. In cases where the catalyst is molded, such as by extrusion with an organic binder, the aluminosilicate can be extruded before drying, or, dried or partially dried and then extruded.

SSZ-48 can be composited with other materials resistant to the temperatures and other conditions employed in organic conversion processes. Such matrix materials include active and inactive materials and synthetic or naturally occurring zeolites as well as inorganic materials such as clays, silica and metal oxides. Examples of such materials and the manner in which they can be used are disclosed in U.S. Pat. No. 4,910,006, issued May 20, 1990 to Zones et al., and U.S. Pat. No. 5,316,753, issued May 31, 1994 to Nakagawa, both of which are incorporated by reference herein in their entirety.

Hydrocarbon Conversion Processes

SSZ-48 zeolites are useful in hydrocarbon conversion reactions. Hydrocarbon conversion reactions are chemical and catalytic processes in which carbon containing compounds are changed to different carbon containing compounds. Examples of hydrocarbon conversion reactions in which SSZ-48 are expected to be useful include hydrocracking, dewaxing, catalytic cracking and olefin and aromatics formation reactions. The catalysts are also expected to be useful in other petroleum refining and hydrocarbon conversion reactions such as isomerizing n-paraffins and naphthenes, polymerizing and oligomerizing olefinic or acetylenic compounds such as isobutylene and butene-1, reforming, isomerizing polyalkyl substituted aromatics (e.g., m-xylene), and disproportionating aromatics (e.g., toluene) to provide mixtures of benzene, xylenes and higher methylbenzenes and oxidation reactions. Also included are rearrangement reactions to make various naphthalene derivatives. The SSZ-48 catalysts may have high selectivity, and under hydrocarbon conversion conditions can provide a high percentage of desired products relative to total products.

SSZ-48 zeolites can be used in processing hydrocarbonaceous feedstocks. Hydrocarbonaceous feedstocks contain carbon compounds and can be from many different sources, such as virgin petroleum fractions, recycle petroleum fractions, shale oil, liquefied coal, tar sand oil, synthetic paraffins from NAO, recycled plastic feedstocks and, in general, can be any carbon containing feedstock susceptible to zeolitic catalytic reactions. Depending on the type of processing the hydrocarbonaceous feed is to undergo, the feed can contain metal or be free of metals, it can also have high or low nitrogen or sulfur impurities. It can be appreciated, however, that in general processing will be more efficient (and the catalyst more active) the lower the metal, nitrogen, and sulfur content of the feedstock.

The conversion of hydrocarbonaceous feeds can take place in any convenient mode, for example, in fluidized bed, moving bed, or fixed bed reactors depending on the types of process desired. The formulation of the catalyst particles will vary depending on the conversion process and method of operation.

Other reactions which can be performed using the catalyst of this invention containing a metal, e.g., a Group VIII metal such platinum, include hydrogenation-dehydrogenation reactions, denitrogenation and desulfurization reactions.

The following table indicates typical reaction conditions which may be employed when using catalysts comprising SSZ-48 in the hydrocarbon conversion reactions of this invention. Preferred conditions are indicated in parentheses.

| Process | Temp., ° C. | Pressure | LHSV |
|---|---|---|---|
| Hydrocracking | 175–485 | 0.5–350 bar | 0.1–30 |
| Dewaxing | 200–475 | 15–3000 psig | 0.1–20 |
|  | (250–450) | (200–3000) | (0.2–10) |
| Aromatics formation | 400–600 (480–550) | atm. −10 bar | 0.1–15 |
| Cat. cracking | 127–885 | subatm. -[1] (atm. −5 atm.) | 0.5–50 |
| Oligomerization | 232–649[2] 10–232[4] (27–204)[4] | 0.1–50 atm.[2,3] — — | 0.2–50[2] 0.05–20[5] (0.1–10)[5] |
| Paraffins to aromatics | 100–700 | 0–1000 psig | 0.5–40[5] |
| Condensation of alcohols | 260–538 | 0.5–1000 psig | 0.5–50[5] |
| Isomerization | 93–538 (204–315) | 50–1000 psig | 1–10 (1–4) |
| Xylene isomerization | 260–593[2] (315–566)[2] 38–371[4] | 0.5–50 atm.[2] (1–5 atm)[2] 1–200 atm.[4] | 0.1–100[5] (0.5–50)[5] 0.5–50 |

[1]Several hundred atmospheres
[2]Gas phase reaction
[3]Hydrocarbon partial pressure
[4]Liquid phase reaction
[5]WHSV Other reaction conditions and parameters are provided below.

Hydrocracking

Using a catalyst which comprises SSZ-48, preferably predominantly in the hydrogen form, and a hydrogenation promoter, heavy petroleum residual feedstocks, cyclic stocks and other hydrocrackate charge stocks can be hydrocracked using the process conditions and catalyst components disclosed in the aforementioned U.S. Pat. No.4,910, 006 and U.S. Pat. No. 5,316,753.

The hydrocracking catalysts contain an effective amount of at least one hydrogenation component of the type commonly employed in hydrocracking catalysts. The hydrogenation component is generally selected from the group of hydrogenation catalysts consisting of one or more metals of Group VIB and Group VIII, including the salts, complexes and solutions containing such. The hydrogenation catalyst is preferably selected from the group of metals, salts and complexes thereof of the group consisting of at least one of platinum, palladium, rhodium, iridium, ruthenium and mixtures thereof or the group consisting of at least one of nickel, molybdenum, cobalt, tungsten, titanium, chromium and mixtures thereof. Reference to the catalytically active metal or metals is intended to encompass such metal or metals in the elemental state or in some form such as an oxide, sulfide, halide, carboxylate and the like. The hydrogenation catalyst is present in an effective amount to provide the hydrogenation function of the hydrocracking catalyst, and preferably in the range of from 0.05 to 25% by weight.

Dewaxing

SSZ-48, preferably predominantly in the hydrogen form, can be used to dewax hydrocarbonaceous feeds by selectively removing straight chain paraffins. Typically, the viscosity index of the dewaxed product is improved (compared to the waxy feed) when the waxy feed is contacted with SSZ-48 under isomerization dewaxing conditions.

The catalytic dewaxing conditions are dependent in large measure on the feed used and upon the desired pour point. Hydrogen is preferably present in the reaction zone during the catalytic dewaxing process. The hydrogen to feed ratio is typically between about 500 and about 30,000 SCF/bbl (standard cubic feet per barrel), preferably about 1000 to about 20,000 SCF/bbl. Generally, hydrogen will be separated from the product and recycled to the reaction zone. Typical feedstocks include light gas oil, heavy gas oils and reduced crudes boiling above about 350° F.

A typical dewaxing process is the catalytic dewaxing of a hydrocarbon oil feedstock boiling above about 350° F. and containing straight chain and slightly branched chain hydrocarbons by contacting the hydrocarbon oil feedstock in the presence of added hydrogen gas at a hydrogen pressure of about 15–3000 psi with a catalyst comprising SSZ-48 and at least one Group VIII metal.

The SSZ-48 hydrodewaxing catalyst may optionally contain a hydrogenation component of the type commonly employed in dewaxing catalysts. See the aforementioned U.S. Pat. No. 4,910,006 and U.S. Pat. No. 5,316,753 for examples of these hydrogenation components.

The hydrogenation component is present in an effective amount to provide an effective hydrodewaxing and hydroisomerization catalyst preferably in the range of from about 0.05 to 5% by weight. The catalyst may be run in such a mode to increase isodewaxing at the expense of cracking reactions.

The feed may be hydrocracked, followed by dewaxing. This type of two stage process and typical hydrocracking conditions are described in U.S. Pat. No. 4,921,594, issued May 1, 1990 to Miller, which is incorporated herein by reference in its entirety.

SSZ-48 may also be utilized as a dewaxing catalyst in the form of a layered catalyst. That is, the catalyst comprises a first layer comprising zeolite SSZ-48 and at least one Group VIII metal, and a second layer comprising an aluminosilicate zeolite which is more shape selective than zeolite SSZ-48. The use of layered catalysts is disclosed in U.S. Pat. No. 5,149,421, issued Sep. 22, 1992 to Miller, which is incorporated herein by reference in its entirety. The layering may also include a bed of SSZ-48 layered with a non-zeolitic component designed for either hydrocracking or hydrofinishing.

SSZ-48 may also be used to dewax raffinates, including bright stock, under conditions such as those disclosed in U.S. Pat. No. 4,181,598, issued Jan. 1, 1980 to Gillespie et al., which is incorporated by reference herein in its entirety.

It is often desirable to use mild hydrogenation (sometimes referred to as hydrofinishing) to produce more stable dewaxed products. The hydrofinishing step can be performed either before or after the dewaxing step, and preferably after. Hydrofinishing is typically conducted at temperatures ranging from about 190° C. to about 340° C. at pressures from about 400 psig to about 3000 psig at space velocities (LHSV) between about 0.1 and 20 and a hydrogen recycle rate of about 400 to 1500 SCF/bbl. The hydrogenation catalyst employed must be active enough not only to hydrogenate the olefins, diolefins and color bodies which may be present, but also to reduce the aromatic content. Suitable hydrogenation catalyst are disclosed in U.S. Pat. No. 4,921,594, issued May 1, 1990 to Miller, which is incorporated by reference herein in its entirety. The hydrofinishing step is beneficial in preparing an acceptably stable product (e.g., a lubricating oil) since dewaxed products prepared from hydrocracked stocks tend to be unstable to air and light and tend to form sludges spontaneously and quickly.

Lube oil may be prepared using SSZ-48. For example, a $C_{20+}$ lube oil may be made by isomerizing a $C_{20+}$ olefin feed over a catalyst comprising SSZ-48 in the hydrogen form and at least one Group VIII metal. Alternatively, the lubricating oil may be made by hydrocracking in a hydrocracking zone a hydrocarbonaceous feedstock to obtain an effluent comprising a hydrocracked oil, and catalytically dewaxing the effluent at a temperature of at least about 400° F. and at a pressure of from about 15 psig to about 3000 psig in the presence of added hydrogen gas with a catalyst comprising SSZ-48 in the hydrogen form and at least one Group VIII metal.

Aromatics Formation

SSZ-48 can be used to convert light straight run naphthas and similar mixtures to highly aromatic mixtures. Thus, normal and slightly branched chained hydrocarbons, preferably having a boiling range above about 40° C. and less than about 200° C., can be converted to products having a substantial higher octane aromatics content by contacting the hydrocarbon feed with a catalyst comprising SSZ-48. It is also possible to convert heavier feeds into BTX or naphthalene derivatives of value using a catalyst comprising SSZ-48.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium or tin or a mixture thereof may also be used in conjunction with the Group VIII metal compound and preferably a noble metal compound. The most preferred metal is platinum. The amount of Group VIII metal present in the conversion catalyst should be within the normal range of use in reforming catalysts, from about 0.05 to 2.0 weight percent, preferably 0.2 to 0.8 weight percent.

It is critical to the selective production of aromatics in useful quantities that the conversion catalyst be substantially free of acidity, for example, by neutralizing the zeolite with a basic metal, e.g., alkali metal, compound. Methods for rendering the catalyst free of acidity are known in the art. See the aforementioned U.S. Pat. No. 4,910,006 and U.S. Pat. No. 5,316,753 for a description of such methods.

The preferred alkali metals are sodium, potassium, rubidium and cesium. The zeolite itself can be substantially free of acidity only at very high silica:alumina mole ratios.

Catalytic Cracking

Hydrocarbon cracking stocks can be catalytically cracked in the absence of hydrogen using SSZ-48, preferably predominantly in the hydrogen form.

When SSZ-48 is used as a catalytic cracking catalyst in the absence of hydrogen, the catalyst may be employed in conjunction with traditional cracking catalysts, e.g., any aluminosilicate heretofore employed as a component in cracking catalysts. Typically, these are large pore, crystalline aluminosilicates. Examples of these traditional cracking catalysts are disclosed in the aforementioned U.S. Pat. No. 4,910,006 and U.S. Pat. No. 5,316,753. When a traditional cracking catalyst (TC) component is employed, the relative weight ratio of the TC to the SSZ-48 is generally between about 1:10 and about 500:1, desirably between about 1:10 and about 200:1, preferably between about 1:2 and about 50:1, and most preferably is between about 1:1 and about 20:1. The novel zeolite and/or the traditional cracking component may be further ion exchanged with rare earth ions to modify selectivity.

The cracking catalysts are typically employed with an inorganic oxide matrix component. See the aforementioned U.S. Pat. No. 4,910,006 and U.S. Pat. No. 5,316,753 for examples of such matrix components.

Isomerization

The present catalyst is highly active and highly selective for isomerizing $C_4$ to $C_7$ hydrocarbons. The activity means that the catalyst can operate at relatively low temperature which thermodynamically favors highly branched paraffins. Consequently, the catalyst can produce a high octane product. The high selectivity means that a relatively high liquid yield can be achieved when the catalyst is run at a high octane.

The present process comprises contacting the isomerization catalyst, i.e., a catalyst comprising SSZ-48 in the hydrogen form, with a hydrocarbon feed under isomerization conditions. The feed is preferably a light straight run fraction, boiling within the range of 30° F. to 250° F. and preferably from 60° F. to 200° F. Preferably, the hydrocarbon feed for the process comprises a substantial amount of $C_4$ to $C_7$ normal and slightly branched low octane hydrocarbons, more preferably $C_5$ and $C_6$ hydrocarbons.

It is preferable to carry out the isomerization reaction in the presence of hydrogen. Preferably, hydrogen is added to give a hydrogen to hydrocarbon ratio ($H_2$/HC) of between 0.5 and 10 $H_2$/HC, more preferably between 1 and 8 $H_2$/HC. See the aforementioned U.S. Pat. No. 4,910,006 and U.S. Pat. No. 5,316,753 for a further discussion of isomerization process conditions.

A low sulfur feed is especially preferred in the present process. The feed preferably contains less than 10 ppm, more preferably less than 1 ppm, and most preferably less than 0.1 ppm sulfur. In the case of a feed which is not already low in sulfur, acceptable levels can be reached by hydrogenating the feed in a presaturation zone with a hydrogenating catalyst which is resistant to sulfur poisoning. See the aforementioned U.S. Pat. No. 4,910,006 and U.S. Pat. No. 5,316,753 for a further discussion of this hydrodesulfurization process.

It is preferable to limit the nitrogen level and the water content of the feed. Catalysts and processes which are suitable for these purposes are known to those skilled in the art.

After a period of operation, the catalyst can become deactivated by sulfur or coke. See the aforementioned U.S. Pat. No. 4,910,006 and U.S. Pat. No. 5,316,753 for a further discussion of methods of removing this sulfur and coke, and of regenerating the catalyst.

The conversion catalyst preferably contains a Group VIII metal compound to have sufficient activity for commercial use. By Group VIII metal compound as used herein is meant the metal itself or a compound thereof. The Group VIII noble metals and their compounds, platinum, palladium, and iridium, or combinations thereof can be used. Rhenium and tin may also be used in conjunction with the noble metal. The most preferred metal is platinum. The amount of Group VIII metal present in the conversion catalyst should be within the normal range of use in isomerizing catalysts, from about 0.05 to 2.0 weight percent, preferably 0.2 to 0.8 weight percent.

Alkylation and Transalkylation

SSZ-48 can be used in a process for the alkylation or transalkylation of an aromatic hydrocarbon. The process comprises contacting the aromatic hydrocarbon with a $C_2$ to $C_{16}$ olefin alkylating agent or a polyalkyl aromatic hydrocarbon transalkylating agent, under at least partial liquid phase conditions, and in the presence of a catalyst comprising SSZ-48.

SSZ-48 can also be used for removing benzene from gasoline by alkylating the benzene as described above and removing the alkylated product from the gasoline.

For high catalytic activity, the SSZ-48 zeolite should be predominantly in its hydrogen ion form. It is preferred that, after calcination, at least 80% of the cation sites are occupied by hydrogen ions and/or rare earth ions.

Examples of suitable aromatic hydrocarbon feedstocks which may be alkylated or transalkylated by the process of the invention include aromatic compounds such as benzene, toluene and xylene. The preferred aromatic hydrocarbon is benzene. There may be occasions where naphthalene derivatives may be desirable. Mixtures of aromatic hydrocarbons may also be employed.

Suitable olefins for the alkylation of the aromatic hydrocarbon are those containing 2 to 20, preferably 2 to 4, carbon atoms, such as ethylene, propylene, butene-1, trans-butene-2 and cis-butene-2, or mixtures thereof. There may be instances where pentenes are desirable. The preferred olefins are ethylene and propylene. Longer chain alpha olefins may be used as well.

When transalkylation is desired, the transalkylating agent is a polyalkyl aromatic hydrocarbon containing two or more alkyl groups that each may have from 2 to about carbon atoms. For example, suitable polyalkyl aromatic hydrocarbons include di-, tri- and tetra-alkyl aromatic hydrocarbons, such as diethylbenzene, triethylbenzene, diethylmethylbenzene (diethyltoluene), di-isopropylbenzene, di-isopropyltoluene, dibutylbenzene, and the like. Preferred polyalkyl aromatic hydrocarbons are the dialkyl benzenes. A particularly preferred polyalkyl aromatic hydrocarbon is di-isopropylbenzene.

When alkylation is the process conducted, reaction conditions are as follows. The aromatic hydrocarbon feed should be present in stoichiometric excess. It is preferred that molar ratio of aromatics to olefins be greater than four-to-one to prevent rapid catalyst fouling. The reaction temperature may range from 100° F. to 600° F., preferably 250° F. to 450° F. The reaction pressure should be sufficient to maintain at least a partial liquid phase in order to retard catalyst fouling. This is typically 50 psig to 1000 psig depending on the feedstock and reaction temperature. Contact time may range from 10 seconds to hours, but is usually from 5 minutes to an hour. The weight hourly space velocity (WHSV), in terms of grams (pounds) of aromatic hydrocarbon and olefin per gram (pound) of catalyst per hour, is generally within the range of about 0.5 to 50.

When transalkylation is the process conducted, the molar ratio of aromatic hydrocarbon will generally range from about 1:1 to 25:1, and preferably from about 2:1 to 20:1. The reaction temperature may range from about 100° F. to 600° F., but it is preferably about 250° F. to 450° F. The reaction pressure should be sufficient to maintain at least a partial liquid phase, typically in the range of about 50 psig to 1000 psig, preferably 300 psig to 600 psig. The weight hourly space velocity will range from about 0.1 to 10. U.S. Pat. No. 5,082,990 issued on Jan. 21, 1992 to Hsieh, et al. describes such processes and is incorporated herein by reference.

Conversion of Paraffins to Aromatics

SSZ-48 can be used to convert light gas $C_2$–$C_6$ paraffins to higher molecular weight hydrocarbons including aromatic compounds. Preferably, the zeolite will contain a catalyst metal or metal oxide wherein said metal is selected from the group consisting of Groups IB, IIB, VIII and IIIA of the Periodic Table. Preferably, the metal is gallium, niobium, indium or zinc in the range of from about 0.05 to 5% by weight.

Xylene Isomerization

SSZ-48 may also be useful in a process for isomerizing one or more xylene isomers in a $C_8$ aromatic feed to obtain ortho-, meta-, and para-xylene in a ratio approaching the equilibrium value. In particular, xylene isomerization is used in conjunction with a separate process to manufacture para-xylene. For example, a portion of the para-xylene in a mixed $C_8$ aromatics stream may be recovered by crystallization and centrifugation. The mother liquor from the crystallizer is then reacted under xylene isomerization conditions to restore ortho-, meta- and para-xylenes to a near equilibrium ratio. At the same time, part of the ethylbenzene in the mother liquor is converted to xylenes or to products which are easily separated by filtration. The isomerate is blended with fresh feed and the combined stream is distilled to remove heavy and light by-products. The resultant $C_8$ aromatics stream is then sent to the crystallizer to repeat the cycle.

Optionally, isomerization in the vapor phase is conducted in the presence of 3.0 to 30.0 moles of hydrogen per mole of alkylbenzene (e.g., ethylbenzene). If hydrogen is used, the catalyst should comprise about 0.1 to 2.0 wt % of a hydrogenation/dehydrogenation component selected from Group VIII (of the Periodic Table) metal component, especially platinum or nickel. By Group VIII metal component is meant the metals and their compounds such as oxides and sulfides.

Optionally, the isomerization feed may contain 10 to 90 wt % of a diluent such as toluene, trimethylbenzene, naphthenes or paraffins.

Oligomerization

It is expected that SSZ-48 can also be used to oligomerize straight and branched chain olefins having from about 2 to 21 and preferably 2–5 carbon atoms. The oligomers which are the products of the process are medium to heavy olefins which are useful for both fuels, i.e., gasoline or a gasoline blending stock and chemicals.

The oligomerization process comprises contacting the olefin feedstock in the gaseous or liquid phase with a catalyst comprising SSZ-48.

The zeolite can have the original cations associated therewith replaced by a wide variety of other cations according to techniques well known in the art. Typical cations would include hydrogen, ammonium and metal cations including mixtures of the same. Of the replacing metallic cations, particular preference is given to cations of metals such as rare earth metals, manganese, calcium, as well as metals of Group II of the Periodic Table, e.g., zinc, and Group VIII of the Periodic Table, e.g., nickel. One of the prime requisites is that the zeolite have a fairly low aromatization activity, i.e., in which the amount of aromatics produced is not more than about 20% by weight. This is accomplished by using a zeolite with controlled acid activity [alpha value] of from about 0.1 to about 120, preferably from about 0.1 to about 100, as measured by its ability to crack n-hexane.

Alpha values are defined by a standard test known in the art, e.g., as shown in U.S. Pat. No. 3,960,978 issued on Jun. 1, 1976 to Givens et al. which is incorporated totally herein by reference. If required, such zeolites may be obtained by steaming, by use in a conversion process or by any other method which may occur to one skilled in this art.

Condensation of Alcohols

SSZ-48 can be used to condense lower aliphatic alcohols having 1 to 10 carbon atoms to a gasoline boiling point hydrocarbon product comprising mixed aliphatic and aromatic hydrocarbon. The process disclosed in U.S. Pat. No. 3,894,107, issued Jul. 8, 1975 to Butter et al., describes the process conditions used in this process, which patent is incorporated totally herein by reference.

The catalyst may be in the hydrogen form or may be base exchanged or impregnated to contain ammonium or a metal cation complement, preferably in the range of from about 0.05 to 5% by weight. The metal cations that may be present include any of the metals of the Groups I through VIII of the Periodic Table. However, in the case of Group IA metals, the cation content should in no case be so large as to effectively inactivate the catalyst, nor should the exchange be such as to eliminate all acidity. There may be other processes involving treatment of oxygenated substrates where a basic catalyst is desired.

Other Uses for SSZ-48

SSZ-48 can also be used as an adsorbent with high selectivities based on molecular sieve behavior and also based upon preferential hydrocarbon packing within the pores.

SSZ-48 may also be used for the catalytic reduction of the oxides of nitrogen in a gas stream. Typically, the gas stream also contains oxygen, often a stoichiometric excess thereof. Also, the SSZ-48 may contain a metal or metal ions within or on it which are capable of catalyzing the reduction of the nitrogen oxides. Examples of such metals or metal ions include copper, cobalt and mixtures thereof.

One example of such a process for the catalytic reduction of oxides of nitrogen in the presence of a zeolite is disclosed in U.S. Pat. No. 4,297,328, issued Oct. 27, 1981 to Ritscher et al., which is incorporated by reference herein. There, the catalytic process is the combustion of carbon monoxide and hydrocarbons and the catalytic reduction of the oxides of nitrogen contained in a gas stream, such as the exhaust gas from an internal combustion engine. The zeolite used is metal ion-exchanged, doped or loaded sufficiently so as to provide an effective amount of catalytic copper metal or copper ions within or on the zeolite. In addition, the process is conducted in an excess of oxidant, e.g., oxygen.

EXAMPLES

The following examples demonstrate but do not limit the present invention.

Example 1

Synthesis of N,N-Diethyldecahydroquinolinium cation (Template A)

A 500 ml. round bottom flask is equipped with a magnetic stir bar and a liquid addition funnel which has a pressure equalization arm. 24.8 Grams of decahydroquinoline (Aldrich, mixture of isomers) and 26 grams of potassium bicarbonate are dissolved in 170 ml of methanol. 67.4 Grams of iodoethane are added dropwise to the solution over a 10–15 minute period. No exotherm is detected. Using a heating mantle for the flask, the solution is slowly brought to reflux and held there for 48 hours. The reaction is cooled to room temperature, the methanol is stripped off, the remaining solids are treated with 250 ml of chloroform and the undissolved solids are filtered away. The chloroform fraction is stripped off, the solids are then recrystallized from a minimum of hot isopropyl alcohol, and the dried solids can be ion-exchanged to the OH form by treatment with BioRad AG 1-X8 OH resin, with the molarity of the product determined by titration.

Example 2

Preparation of Borosilicate SSZ-48 Starting $SiO_2/B_2O_3=50$

Three mmol of a solution of Template A (5.33 grams, 0.562 mmol $OH^-/g$) is mixed with 1.2 grams of 1.0 N NaOH and 5.4 grams of water. Sodium borate decahydrate (0.057 gram) is added to this solution and stirred until all of the solids have dissolved. Cabosil M-5 fumed silica (0.92 gram) is then added to the solution and the resulting mixture is heated at 160° C. and rotated at 43 rpm for 49 days. A settled product results, which is filtered, washed, dried and determined by XRD to be SSZ-48. The product has a $SiO_2/B_2O_3$ mole ratio of 63.

Example 3

The reaction of Example 2 is repeated, with the exception that seed crystals of the SSZ-48 made in Example 2 are added to the reaction mixture. The product is SSZ-48, and is recoverable at 7 days of reaction.

Example 4

1.5 Millimoles of Template A and 0.50 gram of 1N NaOH are combined to make a solution of 8 grams. 0.60 Gram of calcined boron beta zeolite is added as the source of both silicon and boron. The resulting mixture is heated at 150° C. without stirring. SSZ-48 is recovered after 7–9 days of heating.

Example 5

The reaction of Example 4 is repeated, with the exception that 0.10 gram of sodium tetraborate decahydrate is also added. The product is well-crystallized SSZ-48. X-ray diffraction data for this product is shown in Table III below.

TABLE III

| 2 Theta | d | $I/I_2 \times 100$ |
|---|---|---|
| 6.6 | 13.4 | 52 |
| 8.05 | 11.0 | 68 |
| 9.4 | 9.40 | 28 |
| 11.3 | 7.82 | 16 |
| 14.1 | 6.28 | 13 |
| 16.25 | 5.45 | 23 |
| 16.7 | 5.30 | 20 |
| 18.55 | 4.78 | 23 |
| 18.9 | 4.69 | 26 |
| 19.5 | 4.55 | 12 |
| 19.85 | 4.47 | 28 |
| 20.1 | 4.41 | 86 |
| 20.6 | 4.31 | 4 |
| 21.2 | 4.19 | 9 |
| 21.65 | 4.10 | 20 |
| 22.2 | 4.00 | 9 |
| 22.75 | 3.91 | 100 |
| 23.2 | 3.83 | 5 |
| 23.9 | 3.72 | 20 |
| 24.15 | 3.68 | 70 |
| 24.25 | 3.67 | 53 |
| 24.65 | 3.61 | 8 |
| 24.85 | 3.58 | 6 |
| 25.4 | 3.50 | 2 |
| 25.8 | 3.45 | 4 |
| 26.05 | 3.42 | 2 |
| 26.3 | 3.39 | 17 |
| 26.55 | 3.35 | 54 |
| 26.85 | 3.32 | 9 |
| 27.2 | 3.28 | 3 |
| 27.5 | 3.24 | 9 |
| 27.95 | 3.19 | 49 |
| 28.45 | 3.13 | 7 |
| 29.05 | 3.07 | 4 |
| 29.25 | 3.05 | 9 |
| 29.85 | 2.99 | 2 |
| 30.35 | 2.94 | 5 |
| 30.9 | 2.89 | 3 |
| 31.2 | 2.86 | 1 |
| 31.95 | 2.80 | 5 |
| 32.65 | 2.74 | 6 |
| 32.85 | 2.72 | 6 |
| 33.4 | 2.68 | 2 |
| 33.7 | 2.66 | 4 |
| 34.4 | 2.60 | 5 |
| 34.7 | 2.58 | 6 |
| 35.0 | 2.56 | 2 |
| 35.4 | 2.53 | 1 |
| 35.95 | 2.50 | 31 |
| 36.6 | 2.45 | 2 |
| 36.9 | 2.43 | 7 |
| 37.0 | 2.43 | 9 |
| 37.55 | 2.39 | 7 |
| 38.05 | 2.36 | 3 |
| 38.40 | 2.34 | 2 |
| 38.9 | 2.31 | 3 |
| 39.65 | 2.27 | 2 |

Example 6

The components used in Example 4 are scaled up by a factor of 10 and the reaction is run in a 300 cc Parr reactor with internal stirring. After five days at 160° C. and 75 RPM, the product is SSZ-48 with some cristobalite.

Example 7

Calcination of SSZ-48

The material from Example 5 is calcined in the following manner. A thin bed of material is heated in a muffle furnace from room temperature to 120° C. at a rate of 1° C. per minute and held at 120° C. for three hours. The temperature is then ramped up to 540° C. at the same rate and held at this temperature for 5 hours, after which it is increased to 594° C. and held there for another 5 hours. A 10/90 mixture of air and nitrogen is passed over the zeolite at a rate of 20 standard cubic feet per minute during heating. The X-ray diffraction data for the calcined product is shown in Table IV below.

TABLE IV

Calcined SSZ-48

| 2 Theta | d | $I/I_2 \times 100$ |
|---|---|---|
| 6.55 | 13.5 | 93 |
| 8.0 | 11.0 | 100 |
| 9.4 | 9.40 | 45 |
| 11.25 | 7.86 | 26 |
| 14.1 | 6.28 | 3 |
| 16.1 | 5.49 | 5 |
| 16.2 | 5.46 | 3 |
| 16.6 | 5.33 | 6 |
| 18.55 | 4.78 | 6 |
| 18.85 | 4.70 | 12 |
| 19.45 | 4.56 | 8 |
| 19.8 | 4.48 | 11 |
| 20.05 | 4.43 | 55 |
| 21.15 | 4.20 | 2 |
| 21.65 | 4.10 | 13 |
| 22.1 | 4.02 | 5 |
| 22.65 | 3.92 | 47 |
| 23.1 | 3.84 | 3 |
| 23.95 | 3.71 | 12 |
| 24.1 | 3.69 | 25 |
| 24.25 | 3.67 | 24 |
| 24.8 | 3.59 | 2 |
| 25.45 | 3.50 | 2 |
| 25.7 | 3.47 | 1 |
| 26.0 | 3.42 | 2 |
| 26.3 | 3.38 | 8 |
| 26.45 | 3.37 | 21 |
| 26.7 | 3.34 | 4 |
| 27.15 | 3.28 | 1 |
| 27.5 | 3.24 | 2 |
| 27.85 | 3.20 | 13 |
| 28.4 | 3.14 | 2 |
| 29.1 | 3.07 | 5 |
| 29.85 | 2.99 | 1 |
| 30.2 | 2.95 | 1 |
| 30.8 | 2.90 | 1 |
| 31.15 | 2.87 | 1 |
| 31.9 | 2.80 | 2 |
| 32.7 | 2.74 | 3 |
| 33.25 | 2.69 | 1 |
| 33.7 | 2.66 | 2 |
| 34.1 | 2.63 | 1 |
| 34.3 | 2.61 | 4 |
| 34.5 | 2.60 | 2 |
| 35.8 | 2.51 | 13 |
| 36.45 | 2.46 | 2 |
| 36.8 | 2.44 | 3 |
| 37.05 | 2.42 | 3 |
| 37.5 | 2.40 | 3 |
| 38.0 | 2.37 | 1 |
| 38.35 | 2.35 | 1 |
| 38.8 | 2.32 | 2 |
| 39.5 | 2.28 | 1 |

Example 8

$N_2$ Micropore Volume

The product of Example 7 is subjected to a surface area and micropore volume analysis using $N_2$ as adsorbate and via the BET method. The surface area of the zeolitic material is 430 $M^2/g$ and the micropore volume is 0.154 cc/g, thus exhibiting considerable void volume.

Example 9

Preparation of Aluminosilicate SSZ-48

The product of Example 6, after calcination as in Example 7, is slurried into water with $Al(NO_3)_3 \cdot 9H_2O$. The mass ratio of zeolite/Al/water is 1/1.1/50. The solution is heated for three days at 95° C., then washed with 0.01 N HCl, washed with water, filtered and dried.

Example 10

$NH_4$ Exchange

Ion exchange of calcined SSZ-48 material (prepared in Example 7) is performed using ammonium acetate to convert the zeolite from its $Na^+$ form to the $NH_4^+$ form, and, ultimately, the $H^+$ form. Typically, the same mass of ammonium acetate as zeolite is slurried in water at a ratio of 25–50:1 water to zeolite. The exchange solution is heated at 95° C. for 2 hours and then filtered. This procedure can be repeated up to three times. Following the final exchange, the zeolite is washed several times with water and dried. This $NH_4^+$ form of SSZ-48 can then be converted to the $H^+$ form by calcination (as described in Example 7) to 540° C.

Example 11

Constraint Index Determination

The hydrogen form of the zeolite of Example 6 (after treatment according to Examples 7 and 9) is pelletized at 2–3 KPSI, crushed and meshed to 20–40, and then >0.50 gram is calcined at about 540° C. in air for four hours and cooled in a desiccator. 0.50 Gram is packed into a ⅜ inch stainless steel tube with alundum on both sides of the zeolite bed. A Lindburg furnace is used to heat the reactor tube. Helium is introduced into the reactor tube at 10 cc/min. and at atmospheric pressure. The reactor is heated to about 372° C., and a 50/50 (w/w) feed of n-hexane and 3-methylpentane is introduced into the reactor at a rate of 8 $\mu$l/min. Feed delivery is made via a Brownlee pump. Direct sampling into a gas chromatograph begins after 10 minutes of feed introduction. The Constraint Index value is calculated from the gas chromatographic data using methods known in the art, and is found to be 0.25. At 372° C. and 10 minutes on-stream, feed conversion was greater than 35%.

It can be seen that SSZ-48 has high cracking activity, indicative of strongly acidic sites.

Example 12

Use of SSZ-48 To Convert Methanol

The hydrogen form of the zeolite of Example 6 (after treatment according to Examples 7 and 9) is pelletized at 2–3 KPSI, then crushed and meshed to 20–40. 0.50 Gram is loaded into a ⅜ inch stainless steel reactor tube with alundum on the side of the zeolite bed where the feed is introduced. The reactor is heated in a Lindberg furnace to 1000° F. for 3 hours in air, and then the temperature is reduced to 400° C. in a stream of nitrogen at 20 cc/min. A 22.1% methanol feed (22.1 g methanol/77.9 g water) is introduced into the reactor at a rate of 1.31 cc/hr. The conversion at 10 minutes is 100%.

SSZ-48 makes very little light gas and produces considerable liquid product under these conditions. A large proportion of product is due to the formation of durenes, penta- and hexamethylbenzene (see Table C below). Formation of penta- and hexamethylbenzene is again indicative of a large pore zeolite, as the equilibrium diameter of the latter is 7.1 Angstroms (Chang, C. D., "Methanol to Hydrocarbons", Marcel Dekker, 1983).

TABLE C

| Product | Wt % |
| --- | --- |
| Light gases | 2 |
| Xylenes | 4 |
| $C_9$ aromatics | 13 |
| $C_{10}$ aromatics | 34 |
| Pentamethylbenzene | 24 |
| Hexamethylbenzene | 4 |
| Other $C_{10+}$ aromatics | 19 |

What is claimed is:

1. A zeolite having a mole ratio greater than about 40 of an oxide of a first tetravalent element to an oxide of a second tetravalent element which is different from said first tetravalent element, trivalent element, pentavalent element or mixture thereof and having, after calcination, the X-ray diffraction lines of Table II.

2. A zeolite having a mole ratio greater than about 40 of an oxide selected from the group consisting of silicon oxide, germanium oxide and mixtures thereof to an oxide selected from aluminum oxide, gallium oxide, iron oxide, boron oxide, titanium oxide, indium oxide, vanadium oxide and mixtures thereof, and having, after calcination, the X-ray diffraction lines of Table II.

3. A zeolite according to claim 2 wherein the oxides comprise silicon oxide and aluminum oxide.

4. A zeolite according to claim 2 wherein the oxides comprise silicon oxide and boron oxide.

5. A zeolite according to claim 1 wherein said zeolite is predominantly in the hydrogen form.

6. A zeolite according to claim 1 wherein said zeolite is substantially free of acidity.

7. A zeolite having a composition, as synthesized and in the anhydrous state, in terms of mole ratios as follows:

| | |
| --- | --- |
| $YO_2/W_cO_d$ | 40–100 |
| $M_{n/n}/YO_2$ | 0.01–0.03 |
| $Q/YO_2$ | 0.02–0.05 | wherein Y is silicon, germanium or a mixture thereof; W is aluminum, gallium, iron, boron, titanium, indium, vanadium or mixtures thereof; c is 1 or 2; d is 2 when c is 1 or d is 3 or 5 when c is 2; M is an alkali metal cation, alkaline earth metal cation or mixtures thereof; n is the valence of M; and Q is at least one decahydroquinolinium cation.

8. A zeolite according to claim 7 wherein W is aluminum and Y is silicon.

9. A zeolite according to claim 7 wherein W is boron and Y is silicon.

10. A zeolite according to claim 7 wherein Q is a N,N-diethyldecahydroquinolinium cation.

11. A method of preparing a crystalline material comprising an oxide of a first tetravalent element and an oxide of a second tetravalent element which is different from said first tetravalent element, trivalent element, pentavalent element or mixture thereof, said method comprising contacting under crystallization conditions sources of said oxides and a templating agent comprising a decahydroquinolinium cation.

12. The method according to claim 11 wherein the first tetravalent element is selected from the group consisting of silicon, germanium and combinations thereof.

13. The method according to claim 11 wherein the second tetravalent element, trivalent element or pentavalent element is selected from the group consisting of aluminum, gallium, iron, boron, titanium, indium, vanadium and combinations thereof.

14. The method according to claim 13 wherein the second tetravalent element or trivalent element is selected from the group consisting of aluminum, boron, titanium and combinations thereof.

15. The method according to claim 14 wherein the first tetravalent element is silicon.

16. The method according to claim 11 wherein the templating agent is a N,N-diethyldecahydroquinolinium cation.

17. The method of claim 11 wherein the crystalline material has, after calcination, the X-ray diffraction lines of Table II.

18. A process for converting hydrocarbons comprising contacting a hydrocarbonaceous feed at hydrocarbon converting conditions with a catalyst comprising a zeolite having a mole ratio greater than about 40 of an oxide of a first tetravalent element to an oxide of a second tetravalent element which is different from said first tetravalent element, trivalent element, pentavalent element or mixture thereof and having, after calcination, the X-ray diffraction lines of Table II.

19. The process of claim 18 wherein the zeolite is predominantly in the hydrogen form.

20. The process of claim 18 wherein the zeolite is substantially free of acidity.

21. The process of claim 18 wherein the process is a hydrocracking process comprising contacting the catalyst with a hydrocarbon feedstock under hydrocracking conditions.

22. The process of claim 21 wherein the zeolite is predominantly in the hydrogen form.

23. The process of claim 18 wherein the process is a dewaxing process comprising contacting the catalyst with a hydrocarbon feedstock under dewaxing conditions.

24. The process of claim 23 wherein the zeolite is predominantly in the hydrogen form.

25. The process of claim 18 wherein the process is a process for improving the viscosity index of a dewaxed product of waxy hydrocarbon feeds comprising contacting the catalyst with a waxy hydrocarbon feed under isomerization dewaxing conditions.

26. The process of claim 25 wherein the zeolite is predominantly in the hydrogen form.

27. The process of claim 18 wherein the process is a process for producing a $C_{20+}$ lube oil from a $C_{20+}$ olefin feed comprising isomerizing said olefin feed under isomerization conditions over the catalyst.

28. The process of claim 27 wherein the zeolite is predominantly in the hydrogen form.

29. The process of claim 27 wherein the catalyst further comprises at least one Group VIII metal.

30. The process of claim 18 wherein the process is a process for catalytically dewaxing a hydrocarbon oil feedstock boiling above about 350° F. and containing straight chain and slightly branched chain hydrocarbons comprising contacting said hydrocarbon oil feedstock in the presence of added hydrogen gas at a hydrogen pressure of about 15–3000 psi under dewaxing conditions with the catalyst.

31. The process of claim 30 wherein the zeolite is predominantly in the hydrogen form.

32. The process of claim 30 wherein the catalyst further comprises at least one Group VIII metal.

33. The process of claim 30 wherein said catalyst comprises a layered catalyst comprising a first layer comprising the zeolite and at least one Group VIII metal, and a second layer comprising an aluminosilicate zeolite which is more shape selective than the zeolite of said first layer.

34. The process of claim 18 wherein the process is a process for preparing a lubricating oil which comprises:

hydrocracking in a hydrocracking zone a hydrocarbonaceous feedstock to obtain an effluent comprising a hydrocracked oil; and catalytically dewaxing said effluent comprising hydrocracked oil at a temperature of at least about 400° F. and at a pressure of from about 15 psig to about 3000 psig in the presence of added hydrogen gas with the catalyst.

35. The process of claim 34 wherein the zeolite is predominantly in the hydrogen form.

36. The process of claim 34 wherein the catalyst further comprises at least one Group VIII metal.

37. The process of claim 18 wherein the process is a process for isomerization dewaxing a raffinate comprising contacting said raffinate in the presence of added hydrogen under isomerization dewaxing conditions with the catalyst.

38. The process of claim 37 wherein the zeolite is predominantly in the hydrogen form.

39. The process of claim 37 wherein the catalyst further comprises at least one Group VIII metal.

40. The process of claim 37 wherein the raffinate is bright stock.

41. The process of claim 18 wherein the process is a process for increasing the octane of a hydrocarbon feedstock to produce a product having an increased aromatics content comprising contacting a hydrocarbonaceous feedstock which comprises normal and slightly branched hydrocarbons having a boiling range above about 40° C. and less than about 200° C. under aromatic conversion conditions with the catalyst.

42. The process of claim 41 wherein the zeolite is substantially free of acid.

43. The process of claim 41 wherein the zeolite contains a Group VIII metal component.

44. The process of claim 18 wherein the process is a catalytic cracking process comprising contacting a hydrocarbon feedstock in a reaction zone under catalytic cracking conditions in the absence of added hydrogen with the catalyst.

45. The process of claim 44 wherein the zeolite is predominantly in the hydrogen form.

46. The process of claim 44 wherein the catalyst additionally comprises a large pore crystalline cracking component.

47. The process of claim 18 wherein the process is an isomerization process for isomerizing $C_4$ to $C_7$ hydrocarbons, comprising contacting a feed having normal and slightly branched $C_4$ to $C_7$ hydrocarbons under isomerizing conditions with the catalyst.

48. The process of claim 47 wherein the zeolite is predominantly in the hydrogen form.

49. The process of claim 47 wherein the zeolite has been impregnated with at least one Group VIII metal.

50. The process of claim 47 wherein the catalyst has been calcined in a steam/air mixture at an elevated temperature after impregnation of the Group VIII metal.

51. The process of claim 49 wherein the Group VIII metal is platinum.

52. The process of claim 18 wherein the process is a process for alkylating an aromatic hydrocarbon which comprises contacting under alkylation conditions at least a molar excess of an aromatic hydrocarbon with a $C_2$ to $C_{20}$ olefin under at least partial liquid phase conditions and in the presence of the catalyst.

53. The process of claim 52 wherein the zeolite is predominantly in the hydrogen form.

54. The process of claim 52 wherein the olefin is a $C_2$ to $C_4$ olefin.

55. The process of claim 54 wherein the aromatic hydrocarbon and olefin are present in a molar ratio of about 4:1 to about 20:1, respectively.

56. The process of claim 54 wherein the aromatic hydrocarbon is selected from the group consisting of benzene, toluene, ethylbenzene, xylene, or mixtures thereof.

57. The process of claim 18 wherein the process is a process for transalkylating an aromatic hydrocarbon which comprises contacting under transalkylating conditions an aromatic hydrocarbon with a polyalkyl aromatic hydrocarbon under at least partial liquid phase conditions and in the presence of the catalyst.

58. The process of claim 57 wherein the zeolite is predominantly in the hydrogen form.

59. The process of claim 57 wherein the aromatic hydrocarbon and the polyalkyl aromatic hydrocarbon are present in a molar ratio of from about 1:1 to about 25:1, respectively.

60. The process of claim 57 wherein the aromatic hydrocarbon is selected from the group consisting of benzene, toluene, ethylbenzene, xylene, or mixtures thereof.

61. The process of claim 57 wherein the polyalkyl aromatic hydrocarbon is a dialkylbenzene.

62. The process of claim 18 wherein the process is a process to convert paraffins to aromatics which comprises contacting paraffins under conditions which cause paraffins to convert to aromatics with a catalyst comprising the zeolite and gallium, zinc, or a compound of gallium or zinc.

63. The process of claim 18 wherein the process is a process for isomerizing olefins comprising contacting said olefin under conditions which cause isomerization of the olefin with the catalyst.

64. The process of claim 18 wherein the process is a process for isomerizing an isomerization feed comprising an aromatic $C_8$ stream of xylene isomers or mixtures of xylene isomers and ethylbenzene, wherein a more nearly equilibrium ratio of ortho-, meta and para-xylenes is obtained, said process comprising contacting said feed under isomerization conditions with the catalyst.

65. The process of claim 18 wherein the process is a process for oligomerizing olefins comprising contacting an olefin feed under oligomerization conditions with the catalyst.

66. A process for converting lower alcohols and other oxygenated hydrocarbons comprising contacting said lower alcohol or other oxygenated hydrocarbon under conditions to produce liquid products with a catalyst comprising a zeolite having a mole ratio greater than about 40 of an oxide of a first tetravalent element to an oxide of a second tetravalent element which is different from said first tetravalent element, trivalent element, pentavalent element or mixture thereof and having, after calcination, the X-ray diffraction lines of Table II.

67. In a process for the reduction of oxides of nitrogen contained in a gas stream in the presence of oxygen wherein said process comprises contacting the gas stream with a zeolite, the improvement comprising using as the zeolite a zeolite having a mole ratio greater than about 40 of an oxide of a first tetravalent element to an oxide of a second tetravalent element which is different from said first tetravalent element, trivalent element, pentavalent element or mixture thereof and having, after calcination, the X-ray diffraction lines of Table II.

68. The process of claim 67 wherein said zeolite contains a metal or metal ions capable of catalyzing the reduction of the oxides of nitrogen.

69. The process of claim 68 wherein the metal is copper, cobalt or mixtures thereof.

70. The process of claim 68 wherein the gas stream is the exhaust stream of an internal combustion engine.

* * * * *